US008357649B2

(12) United States Patent
Chieffi et al.

(10) Patent No.: US 8,357,649 B2
(45) Date of Patent: Jan. 22, 2013

(54) DELIVERY PARTICLE

(75) Inventors: Andre Chieffi, Tynemouth (GB); Julian David Martin, Newcastle upon Tyne (GB); Nicolas Guillard, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 149 days.

(21) Appl. No.: 12/939,703

(22) Filed: Nov. 4, 2010

(65) Prior Publication Data
US 2011/0107524 A1 May 12, 2011

Related U.S. Application Data

(60) Provisional application No. 61/258,874, filed on Nov. 6, 2009, provisional application No. 61/258,900, filed on Nov. 6, 2009, provisional application No. 61/311,928, filed on Mar. 9, 2010.

(51) Int. Cl.
| C11D 17/00 | (2006.01) |
| C11D 17/06 | (2006.01) |
| C11D 3/33 | (2006.01) |
| C11D 3/36 | (2006.01) |
| C11D 3/50 | (2006.01) |
| C11D 7/36 | (2006.01) |
| C11D 9/44 | (2006.01) |
| C11D 11/00 | (2006.01) |
| D06L 1/00 | (2006.01) |

(52) U.S. Cl. ........ 510/444; 510/445; 510/451; 510/101; 510/349; 510/469; 510/480; 510/488; 510/510; 510/513; 8/137

(58) Field of Classification Search .................. 510/445, 510/101, 444, 451, 349, 480, 489, 488, 510, 510/513, 469; 8/137
See application file for complete search history.

(56) References Cited

U.S. PATENT DOCUMENTS

| 4,430,243 A | 2/1984 | Bragg |
| 4,515,705 A | 5/1985 | Moeddel |
| 4,537,706 A | 8/1985 | Severson, Jr. |
| 4,537,707 A | 8/1985 | Severson, Jr. |
| 4,550,862 A | 11/1985 | Barker et al. |
| 4,561,998 A | 12/1985 | Wertz et al. |
| 4,597,898 A | 7/1986 | Vander Meer |
| 4,655,780 A * | 4/1987 | Chun et al. ............... 8/108.1 |
| 4,731,195 A * | 3/1988 | Olson ................ 252/186.34 |
| 4,968,451 A | 11/1990 | Scheibel et al. |
| 5,486,303 A | 1/1996 | Capeci et al. |
| 5,489,392 A | 2/1996 | Capeci et al. |
| 5,516,448 A | 5/1996 | Capeci et al. |
| 5,565,145 A | 10/1996 | Watson et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,846,922 A * | 12/1998 | Lagnemo et al. ............. 510/375 |
| 5,879,584 A | 3/1999 | Bianchetti et al. |
| 5,902,783 A * | 5/1999 | Lagnemo et al. ............. 510/375 |
| 5,929,022 A | 7/1999 | Velazquez |
| 6,132,558 A | 10/2000 | Dyllick-Brenzinger et al. |
| 6,225,464 B1 | 5/2001 | Hiler, II et al. |
| 6,294,514 B1 | 9/2001 | Welling |
| 6,306,812 B1 | 10/2001 | Perkins et al. |
| 6,326,348 B1 | 12/2001 | Vinson et al. |
| 6,376,445 B1 | 4/2002 | Bettiol et al. |
| 6,544,926 B1 | 4/2003 | Bodmer et al. |
| 6,592,990 B2 | 7/2003 | Schwantes |
| 6,869,923 B1 | 3/2005 | Cunningham et al. |
| 2003/0045446 A1* | 3/2003 | Dihora et al. ................ 510/320 |
| 2003/0109401 A1 | 6/2003 | Housmekerides et al. |
| 2006/0287205 A1 | 12/2006 | Popplewell et al. |
| 2007/0004610 A1* | 1/2007 | Brain et al. ................... 510/130 |
| 2007/0123442 A1 | 5/2007 | Holzner et al. |
| 2007/0138674 A1 | 6/2007 | Anastasiou et al. |
| 2007/0173433 A1* | 7/2007 | Heibel et al. .................. 510/515 |
| 2007/0202063 A1 | 8/2007 | Dihora et al. |
| 2007/0233026 A1 | 10/2007 | Roe et al. |
| 2009/0042759 A1* | 2/2009 | Brain et al. ................... 510/123 |
| 2009/0209661 A1 | 8/2009 | Somerville Roberts et al. |
| 2009/0226529 A1 | 9/2009 | Quellet et al. |
| 2009/0247449 A1 | 10/2009 | Burdis et al. |
| 2009/0293207 A1* | 12/2009 | Guyot et al. ...................... 8/159 |
| 2010/0305021 A1 | 12/2010 | Dykstra |
| 2011/0086788 A1 | 4/2011 | Smets et al. |
| 2011/0110993 A1 | 5/2011 | Chieffi et al. |
| 2011/0110997 A1 | 5/2011 | Cunningham et al. |
| 2011/0111999 A1 | 5/2011 | Smets et al. |

FOREIGN PATENT DOCUMENTS

| EP | 1 533 364 A2 | 5/2005 |
| JP | 1 168337 A | 7/1989 |
| WO | WO 00/32601 A2 | 6/2000 |
| WO | WO 01/41915 A1 | 6/2001 |
| WO | WO 01/87475 A1 | 11/2001 |

OTHER PUBLICATIONS

International Search Report; International Application No. PCT/US2010/055394; date of mailing Feb. 23, 2011; 4 pages.

* cited by examiner

Primary Examiner — Lorna M Douyon
(74) Attorney, Agent, or Firm — Marianne Dressman; Andrew J. Mueller

(57) ABSTRACT

The present application relates to benefit agent delivery compositions comprising a material selected from the group consisting of agglomerates comprising chelant and an encapsulated benefit agent; agglomerates comprising an encapsulated benefit agent having a shell comprising chelant; agglomerates comprising an encapsulated benefit agent having a core comprising chelant and combinations thereof, and processes for making and using such benefit agent delivery compositions.

16 Claims, No Drawings

DELIVERY PARTICLE

CROSS REFERENCE TO RELATED APPLICATIONS

This application claims priority to U.S. Provisional Application Ser. No. 61/258,874, filed Nov. 6, 2009; U.S. Provisional Application Ser. No. 61/258,900, filed Nov. 6, 2009; and U.S. Provisional Application Ser. No. 61/311,928, filed Mar. 9, 2010.

FIELD OF INVENTION

The present application relates to agglomerates/particles comprising encapsulated benefit agents, compositions comprising such agglomerates/particles, and processes for making and using such agglomerates/particles and compositions comprising such agglomerates/particles.

BACKGROUND OF THE INVENTION

Benefit agents, such as perfumes, silicones, waxes, flavors, vitamins and fabric softening agents, are expensive and generally less effective when employed at high levels in personal care compositions, cleaning compositions, and fabric care compositions. As a result, there is a desire to maximize the effectiveness of such benefit agents. One method of achieving this objective is to improve the delivery efficiencies of such benefit agents. Unfortunately, it is difficult to improve the delivery efficiencies of benefit agents as such agents may be lost do to the agents' physical or chemical characteristics, or such agents may be incompatible with other compositional components or the situs that is treated.

In an effort to improve the delivery efficiencies of benefit agents, the industry, in many cases, encapsulates such benefit agents. Unfortunately, in some cases, benefit agents, for example, perfume raw materials and flavors, may degrade over time. This results in decreased efficacy and/or the need for additional amounts of such materials to compensate for the loss.

Accordingly, there is a need for a process and a benefit delivery agent that minimizes or eliminates one or more problems associated with the use of encapsulates.

SUMMARY OF THE INVENTION

The present application relates to benefit agent delivery compositions comprising a material selected from the group consisting of: an agglomerate, particulate and/or extrudate comprising chelant and an encapsulated benefit agent having a core and a shell encapsulating said core; an agglomerate, particulate and/or extrudate comprising chelant and an encapsulated benefit agent having a core and a shell encapsulating said core, such encapsulated benefit agent comprising chelant in its shell and/or core; an agglomerate, particulate and/or extrudate comprising an encapsulated benefit agent having a core and a shell encapsulating said core, such encapsulated benefit agent comprising chelant in its shell and/or core and combinations thereof, and processes for making and using such benefit agent delivery compositions.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "chelating agent" means an agent capable of forming a complex with a metal ion.

As used herein, the term "polidentate-type chelant" means a chelant capable of complexing with a metal ion at two or more points.

As used herein, the term "fabric care composition" includes, unless otherwise indicated, fabric softening compositions, fabric enhancing compositions, fabric freshening compositions and combinations there of.

As used herein, the terms "encapsulated benefit agent" and "benefit agent containing delivery particle" are synonymous, and the terms "capsule" and "microcapsule" are synonymous.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Benefit Agent Delivery Composition—Agglomerate/Particle/Extrudate

Applicants have recognized that particular materials used as benefit agents—in particularly those materials that comprise aldehyde moieties, for example, certain perfumes and flavors—when encapsulated, degrade at unexpectedly higher rates. Without being bound by theory, Applicants believe that such material degradation may be the result of oxidation by oxygen in the presence of catalytic materials. For example, Applicants believe that perfume raw material degradation may be the result of oxidation by oxygen in the presence of metal catalysts such as Fe. Specifically, Applicants believe that $Fe_2O_3$—which can be a common impurity in silica used to prepare encapsulates such as those described herein—may result in Fe catalysis of the oxidation of aldehyde to carboxylic acid by oxygen, resulting in the degradation of encapsulated aldehyde-containing materials. Applicants have recognized that, by addition of a chelant, such degradation may be significantly reduced.

In one aspect, a benefit agent delivery compositions comprising a material selected from the group consisting of: an agglomerate, particulate and/or extrudate comprising chelant and an encapsulated benefit agent having a core and a shell encapsulating said core; an agglomerate, particulate and/or extrudate comprising chelant and an encapsulated benefit agent having a core and a shell encapsulating said core, such encapsulated benefit agent comprising chelant in its shell and/or core; an agglomerate, particulate and/or extrudate comprising an encapsulated benefit agent having a core and a shell encapsulating said core, such encapsulated benefit agent comprising chelant in its shell and/or core and combinations thereof, is disclosed.

In one aspect, a benefit agent delivery composition that may be an agglomerate, particulate and/or extrudate that may comprise, based on total benefit agent delivery weight:

a.) from about 2% to about 97%, from about 10% to about 90%, from about 15% to about 85%, from about 20% to about 80%, from about 25% to about 75%, or even from about 30% to about 70% of an encapsulated benefit agent, said encapsulated benefit agent comprising a core and a shell encapsulating said benefit agent, said encapsulated benefit agent comprising a sufficient amount of benefit agent to provide, based on total benefit delivery composition weight from about 1% to about 85%, from about 8% to about 80%, from about 12% to about 75%, from about 15% to about 65%, from about 20% to about 60%, or even from about 25% to about 55% benefit agent;

b.) a chelating agent, said chelant being present in said benefit agent delivery composition, and/or in the shell and/or core of said encapsulated benefit agent;

c.) from about 1% to about 50%, from about 2% to about 45%, from about 3% to about 40%, from about 4% to about 37%, from about 5% to about 35%, or even from about 6% to about 30% of a plasticizer;

d.) from about 1% to about 50%, from about 2% to about 45%, from about 3% to about 35%, from about 4% to about 30%, from about 5% to about 25%, or even from about 6% to about 20% of a binder; and e.) optionally, from about 1% to about 50%, from about 2% to about 45%, from about 5% to about 40%, from about 7% to about 35%, from about 9% to about 30%, or even from about 10% to about 27% of a dusting agent is disclosed.

In one aspect of the aforementioned benefit agent delivery composition, said encapsulated benefit agent may comprise a perfume microcapsule, a binder and mixtures thereof. In one aspect, said perfume microcapsule may comprise a shell, said shell comprising cross-linked melamine formaldehyde.

In one aspect of the aforementioned benefit agent delivery composition a.) said encapsulated benefit agent may comprise a perfume microcapsule, said perfume microcapsule comprising a core and a shell encapsulating said core, said shell and/or core comprising cross-linked melamine formaldehyde and a chelating agent;

b.) said plasticizer may comprise water;

c.) said binder may be selected from the group consisting of celluloses including methylcellulose, including CMC, and derivatives thereof; alginate and derivatives thereof; starches; polyvinyl alcohols; polyethylene oxide; polyvinylpyrrolidone; polysaccharides including chitosan and/or natural gums including carrageenan; polyacrylates including cross-linked polyacrylates; waxes; polyethylene glycols for example, polyethylene glycols having a molecular weight (weight average) of greater than 4000 Da or even from about 4000 Da to about 15,000 Da; alcohol ethoxylates; surfactants and mixtures thereof; and d.) said dusting agent may be selected from the group consisting of silicas; zeolites; amorphous aluminosilicates; clays; starches; celluloses; water soluble salts including sodium chloride, sodium sulphate, magnesium sulphate and/or sodium carbonate; polysaccharides including sugars; and mixtures thereof.

In one aspect, any of the benefit agent delivery compositions disclosed in the present specification may comprise an encapsulated benefit agent that may comprise a benefit agent selected from the group consisting of perfumes; brighteners; insect repellants; silicones; waxes; flavors; vitamins; fabric softening agents; skin care agents including paraffins; enzymes; anti-bacterial agents; bleaches; and mixtures thereof. In one aspect, the encapsulated benefit agent is a perfume comprising an aldehyde.

In one aspect, any of the benefit agent delivery compositions disclosed in the present specification may comprise a chelant selected from the group consisting of chelants comprising a polidentate comprising a soft base; chelants comprising a polidentate that does not comprise a soft base; and combinations thereof.

In one aspect, any of the benefit agent delivery compositions disclosed in the present specification may comprise a chelant comprising a polidentate comprising a soft base, as determined by the Lewis definition of atoms with a lone electron pair in the highest occupied molecular orbital. In this aspect, said chelant comprising a polidentate comprising a soft base may be present in an amount of from about 0.0001% to about 10%, or from about 0.01% to about 0.1%, based on total weight of the agglomerate. In one aspect, said polidentate comprising a soft base may comprise a material selected from the group consisting of polyamines (e.g. dietheylenetriamine, triethylenetriamine, polyethyleneimines); aminoalcohols (e.g., triethanolamine, N-hydroxyethylethylene-diamine, aminoethylethanolamine (AEEA); aminocarboxylic acids, (e.g., ethylenediaminetetraaceticacid (EDTA), diethylenetriaminepenta(methylene phosphonic acid) (DTPMP), diethylenetriaminepentaaceticacid (DTPA), ethylenediamine, diethylene triamine, ethylenediaminedisuccinic acid (EDDS), N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP)) and combinations thereof. In one aspect, the polidentate comprising a soft base may comprise ethylenediaminedisuccinic acid.

In one aspect, any of the benefit agent delivery compositions disclosed in the present specification may comprise a chelant comprising a polidentate that does not comprise a soft base, wherein said chelant comprising a polidentate that does not comprise a soft base may be present in an amount of from about 0.01% to about 50%, or from about 0.1% to about 5%, based on total weight of the agglomerate. In one aspect, said polidentate-type chelant that does not comprise a soft base may comprise a material selected from the group consisting of acrylic polymers, hydroxycarboxylic acids (e.g., tartaric acid, citric acid, malic acid, gluconic acid, ferulic acid, lactic acid, glucuronic acid); 1,3-diketones (e.g., ascorbic acid) polyphosphates (e.g., citric acid, dicarboxymethylglutamic acid, malic acid, nitrilotriacetic acid, oxalic acid, phosphoric acid, succinic acid), and combinations thereof.

In one aspect, chelants that are useful in the benefit agent delivery compositions disclosed in the present specification may comprise a peptide and/or a polar amino acid. Polar amino acid may include arginine, asparagine, aspartic acid, glutamic acid, glutamine, lysine, and combinations thereof.

In one aspect, any of the benefit agent delivery compositions disclosed in the present specification may comprise a chelant that is acceptable for use in products that are edible by humans and/or other animals. Such chelants include polyphosphates (e.g., sodium tripolyphosphate, hexametaphosphoric acid, sodium acid pyrophosphate, sodium pyrophosphate, tetra sodium pyrophosphate, sodium hexametaphosphate, sodium metaphosphate); aminocarboxylic acids (e.g., ethylenediaminetetraacetic acid (EDTA), 1,2-bis(2-amino-phenoxy)ethane-N,N,N'N'-tetraacetic acid (EGTA), ethylenebis(oxyethylenenitrilo)-tetraacetic acid (BAPTA), N-(hydroxyethyl)-ethylenediaminetriacetic acid (HEDTA), diethylene-triaininepentaacetic acid (DTPA), N-dihydroxyethylglycine (2-HxG), ethylenebis(hydroxyphenyl-glycine) (EHPG), glutamic acid, aspartic acid, glycine, lysine); 1,3-diketones (e.g., ascorbic acid); hydroxycarboxylic acids (e.g., tartaric acid, citric acid, malic acid, gluconic acid, ferulic acid, lactic acid, glucuronic acid); polyamines (e.g., dietheylenetriamine, triethylenetriamine); aminoalcohols (e.g., triethanolamine, N-hydroxyethylethylene-diamine, aminoethylethanolamine (AEEA); polymers (e.g., polyethyleneimines, polymethacryloylacetone, poly(p-vinylbenzyliminodiacetic acid)), phosphonic and bisphosphonic acids (e.g., nitrilotrimethylenephosphonic acid, ethylenediaminetetra-dnethylenephosphonic acid), hydroxyethylidenediphosphonic acid) and mixtures thereof.

In one aspect of the aforementioned benefit agent delivery composition said plasticizer may comprise a material selected from the group consisting of water; alcohols including glycerol, ethanol and/or propan-1-diol; glycols including polyethylene glycols, for example, polyethylene glycols having a molecular weight (weight average) of less than 600 Da or even from about 600 Da to about 200 Da; fatty acids; petroleum derivatives including paraffins, petrolatum and/or mineral oils; vegetable oils; and mixtures thereof; in one aspect, said plasticizer may comprise a material selected from the group consisting of water and alcohols and mixtures thereof; in one aspect, said plasticizer may comprise a material selected from the group consisting of water and glycerol and mixtures thereof; in one aspect, said plasticizer may comprise water.

In one aspect of the aforementioned benefit agent delivery composition said binder may comprise a material selected from the group consisting of celluloses including methylcellulose, including CMC, and derivatives thereof; alginate and derivatives thereof; starches; polyvinyl alcohols; polyethylene oxide; polyvinylpyrrolidone; polysaccharides including chitosan and/or natural gums including carrageenan; polyacrylates including cross-linked polyacrylates; waxes; polyethylene glycols for example, polyethylene glycols having a molecular weight (weight average) of greater than 4000 Da or even from about 4000 Da to about 15,000 Da; alcohol ethoxylates; surfactants and mixtures thereof; in one aspect, said binder may comprise a material selected from the group consisting of celluloses including methylcellulose, including CMC, and derivatives thereof; alginate and derivatives thereof; starches; polyvinyl alcohols; polysaccharides including chitosan and/or natural gums including carrageenan; polyacrylates including cross-linked polyacrylates; polyethylene glycols for example, polyethylene glycols having a molecular weight (weight average) of greater than 4000 Da or even from about 4000 Da to about 15,000 Da; and mixtures thereof; in one aspect said binder may comprise a material selected from the group consisting of celluloses including methylcellulose, including CMC, and derivatives thereof; alginate and derivatives thereof; starches; polyvinyl alcohols; polyacrylates including cross-linked polyacrylates; polyethylene glycols for example, polyethylene glycols having a molecular weight (weight average) of greater than 4000 Da or even from about 4000 Da to about 15,000 Da; and mixtures thereof; in one aspect said binder may comprise a material selected from the group consisting of celluloses including methylcellulose, including CMC; polyacrylates including cross-linked polyacrylates; polyethylene glycols for example, polyethylene glycols having a molecular weight (weight average) of greater than 4000 Da or even from about 4000 Da to about 15,000 Da; and mixtures thereof.

In one aspect of the aforementioned benefit agent delivery composition, said dusting agent may comprise a material selected from the group consisting of silicas; zeolites; amorphous aluminosilicates; clays; starches; celluloses; water soluble salts including sodium chloride, sodium sulphate, magnesium sulphate and/or sodium carbonate; polysaccharides including sugars; and mixtures thereof; in one aspect dusting agent may comprise a material selected from the group consisting of silicas; aluminosilicates including zeolite; clays; starches; celluloses; polysaccharides including sugars; and mixtures thereof; in one aspect said dusting agent may comprise a material selected from the group consisting of silicas; aluminosilicates including zeolite; clays; starches; celluloses; and mixtures thereof; in one aspect said dusting agent may comprise a material selected from the group consisting of silicas; aluminosilicates including zeolite; clays; and mixtures thereof.

In any aspect of the aforementioned benefit agent delivery compositions, said agglomerate, extrudate and/or particulate may have a characteristic dimension of about 100 microns to about 3000 microns, from about 200 microns to about 2500 microns, from about 300 microns to about 2000 microns, from about 400 microns to about 1400 microns, or even from about 500 microns to about 1200 microns, wherein for said agglomerates and particulates said characteristic dimension is the median particle size of said agglomerates and particulates and the characteristic dimension of said extrudates is the mean diameter of said extrudates.

Benefit Agent Delivery Composition—Agglomerate/Particle/Extrudate

The benefit agent delivery compositions may be made in accordance with the examples of the present specification and/or by the following process which may comprise:
 a. combining an encapsulated benefit agent, in one aspect, said encapsulated benefit agent comprising a core and a shell encapsulating said core, said encapsulated benefit agent's core and/or shell comprising chelant; a chelant, a plasticizer, and a binder to form a mixture;
 b. combining said mixture with said dusting agent to form a material; and
 c. removing a sufficient amount of said plasticizer from said material to yield a product comprising, based on total product weight from about 1% to about 50%, from about 2% to about 45%, from about 3% to about 40%, from about 4% to about 37%, from about 5% to about 35%, or even from about 6% to about 30% plasticizer.

Encapsulated Benefit Agent

Applicants recognized that the problems associated of incorporating an encapsulated benefit agent into a dry product, including the premature rupturing of the shell of the encapsulated during the incorporation process, can be minimized when the encapsulated benefit agent is further processed and incorporated into an agglomerate that can then be added to a consumer product such as a dry consumer product that may be a particulate, powder or other essentially dry form.

The wall materials of useful encapsulates may comprise materials selected from the group consisting of polyethylenes, polyamides, polystyrenes, polyisoprenes, polycarbonates, polyesters, polyacrylates, polyureas, polyurethanes, polyolefins, polysaccharides, epoxy resins, vinyl polymers, and mixtures thereof. In one aspect, useful wall materials include materials that are sufficiently impervious to the core material and the materials in the environment in which the encapsulated benefit agent will be employed, to permit the delivery benefit to be obtained. Suitable impervious wall materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates and mixtures thereof. In one aspect, the wall material may comprise melamine cross-linked with formaldehyde.

The core of the encapsulated benefit agent may comprise perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers and anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers and mixtures thereof. In one aspect, said perfume raw material may be selected from the group consisting of alcohols, ketones, aldehydes, esters, ethers, nitriles alkenes. In one aspect the core material may comprise a perfume. In one aspect, said perfume may comprise perfume raw materials selected from the group consisting of alcohols, ketones, aldehydes, esters, ethers, nitriles alkenes and mixtures thereof. In one aspect, said perfume may comprise a perfume raw material selected from the group consisting of perfume raw materials having a boiling point (B.P.) lower than about 250° C. and a ClogP lower than about 3, perfume raw materials having a B.P. of greater than about 250° C. and a ClogP of greater than about 3, perfume raw materials having a B.P. of greater than about 250° C. and a ClogP lower than about 3, perfume raw materials having a B.P. lower than about 250° C. and a ClogP greater than about 3 and mixtures thereof. Perfume raw materials having a boiling point B.P. lower than about 250° C. and a ClogP lower than about 3 are known as Quadrant I perfume raw materials, perfume raw materials having a B.P. of greater than about 250° C. and a ClogP of greater than about 3 are known as Quadrant IV perfume raw materials, perfume raw materials having a B.P. of greater than about 250° C. and a ClogP lower than about 3 are known as Quadrant II perfume raw materials, perfume raw materials having a B.P. lower than about 250° C. and a ClogP greater than about 3 are known as a Quadrant III perfume raw materials. In one aspect, said perfume may comprise a perfume raw material having B.P. of lower than about 250° C. In one aspect, said perfume may comprise a perfume raw material selected from the group consisting of Quadrant I, II, III perfume raw materials and mixtures thereof. In one aspect, said perfume may comprise a Quadrant III perfume raw material. Suitable Quadrant I, II, III and IV perfume raw materials are disclosed in U.S. Pat. No. 6,869,923 B1.

In one aspect, said perfume may comprise a Quadrant IV perfume raw material. While not being bound by theory, it is believed that such Quadrant IV perfume raw materials can improve perfume odor "balance". Said perfume may comprise, based on total perfume weight, less than about 30%, less than about 20%, or even less than about 15% of said Quadrant IV perfume raw material.

In one aspect, useful perfumes and/or flavors include those listed in the following Table:

3-(METHYLTHIO)HEXANOL

1-BUTANOL, 2-METHYL-
1-BUTANOL, 3-METHYL-
1-ETHYL PROPYL ACETATE

1-HEXANOL, 2-ETHYL-
1-HEXENOL
1-METHOXY-4-PROPENYLBENZENE

1-METHYL BUTYL ACETATE
1-METHYL PROPYL ACETATE
1-OCTANOL
1-OCTEN-3-OL
2,4-DECADIENAL
2,4-DECADIENOATE
2,5-DIMETHYL-4-HYDROXY-3-(2H)-FURANONE
2,5-DIMETHYLPYRAZINE
-2,5-DIMETHYLPYRAZINE
2,6 DIMETHYL-5 HEPTENAL
2,6-DIMETHYLPYRAZINE

-2,6-DIMETHYLPYRAZINE
2,6-NONADIENAL 2,6-NONADIENAL
2-ACETYL FURAN
2-ACETYL PYRIDINE
-2-ACETYL PYRIDINE
2-ACETYLTHIAZOLE
2-BUTENAL
2-ETHYL-1-HEXANOL

2-HEXANOL
2-ISOPROPYL-4-METHYLTHIAZOLE
2-METHOXY-3-METHYLPYRAZINE

-2-METHOXY-3-METHYLPYRAZINE
2-METHOXY-4-ALLYLPHENOL
2-METHOXYPHENOL
2-METHYL BUTANOL

2-METHYL BUTYLACETATE
2-METHYL PENTENOIC ACID (STRAWBERIFF)
2-METHYL PROPYL ACETATE
2-METHYL-1-PROPANOL
2-METHYL-3-(P-METHYL PHENYL) PROPANAL
2-METHYL-4-PROPYL-1,3-OXATHIANE
2-METHYLBUTANOIC ACID
2-METHYLBUTYL ACETATE
2-METHYLBUTYRIC ACID
2-METHYLPENT-2-ENAL (TRANS)
2-METHYLPROPANOL
2-METHYLPROPYL CAPROATE (ISOBUTYL CAPROATE)
2-METHYLTETRAHYDROFURAN-3-ONE
2-PHENYLETHANOL
2-PROPENOIC ACID, ETHYL ESTER
2-PROPENYL HEXANOATE
3-(METHYLTHIO)-1-PROPANOL
3,4-DIHYDROCOUMARIN
3,5,5-TRIMETHYL HEXANAL
3-METHYL BUTANAL
3-METHYL BUTYL ACETATE
3-METHYLBUTANOL
BETA-PINENE

BUTANAL
BUTANOIC ACID, 2-METHYL-, ETHYL ESTER
BUTANOIC ACID, METHYL ESTER
BUTANOL
BUTYL ACETATE
BUTYL BUTYRATE
BUTYL CAPROATE
BUTYL HEXANOATE
BUTYL PROPIONATE
BUTYRIC ACID

3-METHYLBUTYL ACETATE
3-METHYLBUTYL-2-METHYLBUTYRATE
3-METHYLPROPANAL
3-METHYLTHIO-1-HEXANOL
4-ACETOXY-2,5-DIMETHYL-3(2H)-FURANONE
4-CARVOMENTHANOL
4-METHYL-4-MERCAPTO-2-PENTANONE
4-METHYL-5-THIAZOLEETHANOL
4-METHYLACETOPHENONE
4-TERPINEOL
6 METHYL 5 HEPTENE 2 ONE
6 NONEN 1 OL
6-METHYLHEPT-5EN-2-ONE

A-AMYL CINNAMIC ALDEHYDE
A-BISABOLENE
ACETAL
ACETALDEHYDE
ACETIC ACID
ACETIC ACID, 2-PHENYLETHYL ESTER
ACETOPHENONE
ACETOXY-FURANEOL(4-ACETOXY-2,5-DIMETHYL-(2H)-FURANONE)
ACETYL METHYL CARBINOL
ACETYL PROPIONYL
ALDEHYDE C12
ALDEHYDE C16
ALLYL CAPROATE
ALLYL CYCLOHEXANEPRIOPIONATE
ALPHA-IRONE
ALPHA-IONONE
ALPHA-IRONE
ALPHA-METHYL BENZYL ACETATE
ALPHA-PINENE
ALPHA-TERPINEOL
AMBRETTOLIDE
A-METHYL BENZYL PROPIONATE
AMYL ACETATE
AMYL CINNAMIC ALDEHYDE
AMYL ISOVALERATE
AMYL PROPIONATE
AMYL VALEATE
ANISIC ALDEHYDE
ANISYL ACETATE
ANISYL ACETONE
A-PINENE
ARUSCOL FIRMENICH
B-CARYOPHYLLENE

BENZALDEHYDE
BENZYL ACETATE
BENZYL ALCOHOL
BENZYL ALCOHOL
BENZYL CINNAMATE
BENZYL PROPIONATE
BETA DAMASCENONE
BETA.-DAMASCENONE
BETA-DAMASCONE
BETA-IONONE
ETHYL BUTYRATE
ETHYL CAPRYLATE (OCTANOATE)
ETHYL CINNAMATE
ETHYL DODECANOATE
ETHYL HEXANOATE
ETHYL ISOBUTYRATE
ETHYL ISOVALERATE
ETHYL LACTATE
ETHYL MALTOL
ETHYL MALTOL ™
ETHYL NONANOATE

-continued

| | |
|---|---|
| CAPROIC (HEXANOIC) ACID | ETHYL OCTANOATE |
| CAPRYLIC ACID | ETHYL OCTANOATE |
| CARYOPHYLLENE OXIDE | ETHYL OXYHDRATE |
| | ETHYL PELARGONATE |
| CINNAMIC ALDEHYDE | (NONANOATE) |
| CIS-3-HEXENOL | ETHYL PROPIONATE |
| CIS-3-HEXENYL 2 METHYL BUTYRATE | ETHYL PROPIONATE |
| CIS-3-HEXENYL ACETATE | ETHYL VALERATE |
| CIS-3-HEXENYL ACETATE | 3-ETHOXY-4- |
| | HYDROXYBENZALDEHYDE |
| | (ETHYL VANILLIN) |
| CIS3-HEXENYL BUTYRATE | ETHYL(METHYLTHIO)ACETATE |
| CIS-3-HEXENYL FORMATE | ETHYL-2,5- |
| | (2,6)DIMETHYLPYRAZINE |
| CIS-3-HEXENYL LACTATE | ETHYL-2-METHYLBUTYRATE |
| CIS-3-HEXENYL-2-METHYLBUTYRATE | ETHYL- |
| | 3(METHYLTHIO)PROPIONATE |
| CIS-5-OCTENYL PROPIONATE | ETHYL-3-METHYLBUTYRATE |
| CIS-6-NONENOL | ETHYL-3-METHYLBUTYRATE |
| CIS-JASMONE | ETHYLPHENYL ACETATE |
| CIS-PARA-MENTHA-8-THIOL-3-ONE | FURANEOL ™ |
| (THIOMENTHONE) | |
| CITRAL | GALBANOLENE SUPER |
| CITRONELLOL | GAMMA HEPTALACTONE |
| CITRONELLOL | GAMMA HEXALACTONE |
| CITRONELLYL FORMATE | GAMMA NONALACTONE |
| CITRONELLYL PROPIANOATE | GAMMA OCTALACTONE |
| CYCLAMEN ALDEHYDE | GAMMA UNDECALACTONE |
| CYCLOTENE ™ | GAMMA.-TERPINENE |
| CYMENE | GAMMA-DEACLACTONE |
| DAMASCENONE | GAMMA-DODECALACTONE |
| DECANAL | GAMMA-METHYL IONONE |
| DECANOIC ACID | GERANIOL |
| DECANOL | GERANYL ACETATE |
| DELTA-DODECALATONE | GERANYL BUTYRATE |
| DELTA DECALACTONE | GERANYL FORMATE |
| DELTA OCTALACTONE | GERANYL PROPIONATE |
| DELTA UNDECALACTONE | GLACIAL ACETIC ACID |
| DELTA-DODECALACTONE | G-TERPINENE |
| DIACETYL | HEDIONE |
| DIACETYL | HELIOTROPINE |
| DIMETHYL ANTHRANILATE | HEXANAL |
| DIMETHYL SULFIDE | HEXANOIC ACID |
| | HEXANOIC ACID, METHYL |
| D-LIMONENE | ESTER |
| DODECANAL | HEXANOL |
| DODECANOIC ACID | HEXENYL HEXANOATE |
| ETHYL ACETATE | HEXYL ACETATE |
| ETHYL PENTANOATE | HEXYL ALCOHOL |
| ETHYL 3-(METHYLTHIO)PROPANOATE | HEXYL BUTYRATE |
| ETHYL ACETOACETATE | HEXYL VALERATE |
| ETHYL ACRYLATE | HEXYL-2-METHYLBUTYRATE |
| ETHYL ANTHRANILATE | HYDROXCITRONELLAL |
| ETHYL BENZOATE | HYDROXYACETOPHENONE |
| IRISONE-ALPHA | PALMITIC ACID |
| ISOAMYL ACETATE | PARA-CYMENE |
| ISOAMYL ALCOHOL | PENTANOIC ACID |
| ISOAMYL BUTYRATE | PHENOXYETHYLPROPIONATE |
| ISOBORNYL ACETATE | PHENYL ACETALDEHYDE |
| ISOBUTYL ACETATE | PHENYL ETHANOL |
| ISOBUTYL ACETATE | PHENYL ETHYL ACETATE |
| ISOBUTYL BUTENOATE | PHENYL ETHYL TIGLATE |
| ISOBUTYL CAPROATE | PHENYLETHYL ACETATE |
| ISOBUTYL ISOVALERATE | PHENYLETHYL METHYL ETHER |
| | P-MENTHA-3-ONE-8- |
| ISOBUTYL PHENYL ACETATE | THIOLACETATE |
| ISOPROPYL-4-METHYLTHIAZOLE | PRENOL |
| ISOPULEGOL | PRENYL ACETATE |
| ISOVALERALDEHYDE | PROPANOL |
| LAURINE | PROPIONIC ACID |
| L-CARVONE | PROPYL ACETATE |
| LINALOOL | PROPYLENE GLYCOL |
| LINALOOL OXIDE | PULEGONE |
| LINALYL ACETATE | SULFOX FIRMENICH |
| LINALYL CINNAMATE | TERPENYL ACETATE |
| LINALYL PROPIONATE | THIAZOLE, 2-ETHYL-4-METHYL- |
| LINALYL-3-METHYLBUTYRATE | THIAZOLE, 4-ETHYL-2-PROPYL- |
| L-MENTHONE | THIOMENTHONE |
| MALTOL | THIOMENTHONE ACETATE |
| MALTOL ™ | TRANS-2-CIS-6-NONADIEN-1-OL |

| | | |
|---|---|---|
| MELONAL ™ (SAME AS A18) | | TRANS-2-DECEN-1-AL |
| METHOXY PHENYL BUTANONE | | TRANS-2-HEXENAL |
| METHYL 3(METHYLTHIO)PROPIONATE | | TRANS-2-HEXENAL |
| METHYL AMYL KETONE | | TRANS-2-HEXENOIC ACID |
| METHYL ANTHRANILATE | | TRANS-2-HEXENOL |
| METHYL BUTYRATE | | TRANS-2-HEXENYL ACETATE |
| METHYL CINNAMATE | | TRANS-3-HEXENOIC ACID |
| METHYL HEPTINE CARBONATE | | TRIACETIN |
| METHYL HEPTYL KETONE | | -TRIMETHYLOXAZOLE |
| METHYL HEXYL KETONE | | TRIMETHYLOXAZOLE |
| METHYL THIOBUTYRATE | | TRIMETHYLPYRAZINE |
| METHYL THIOHEXANOL | | -TRIMETHYLPYRAZINE |
| | | 4-HYDROXY-3- |
| METHYL VINYLTHIAZOLE | | METHOXYBENZALDEHYDE |
| | | (VANILLIN) |
| -METHYL VINYLTHIAZOLE | | MYCENE |
| METHYL-2-(METHYLTHIO)ACETATE | | NATACTONE FIMENICH |
| METHYL-2-METHYLBUTYRATE | | N-BUTYRALDEHYDE |
| METHYL-2-OCTYNOATE | | NEROL |
| METHYL-3-METHYLTHIOPROPIONATE | | NERYL ACETATE |
| METHYL-3-NONENOATE | | NONANOL |
| METHYLPHENYL HEXENAL (COCAL ™) | | N-VALERALDEHYDE |
| METHYLTHIO METHYLBUTYRATE | | OCIMENE (TRANS) |
| OCTYL ACETATE | | OCTANAL |
| OXANONE ™ | | OCTANOIC ACID |

Suitable perfumes for use herein include the following:

| CAS | P&G Name | Chemical Name |
|---|---|---|
| 7540-51-4 | BARANOL | (-)-Citronellol |
| 2216-51-5 | MENTHOL | (-)-Menthol |
| 16356-11-9 | GALBANOLENE SUPER | (3E,5Z)-1,3,5-Undecatriene |
| 557-48-2 | E,Z-2,6-NONADIEN-1-AL FCC | (E)-2,(Z)-6-Nonadienal |
| 3239-35-8 | TANGERINOL | (E)-5-Tangerinol |
| 3239-37-0 | TANGERINOL | (Z)-5-Tangerinol |
| 6790-58-5 | AMBROFIX | [3aR-(3aa,5ab,9aa,9bb)]-dodecahydro-3a,6,6,9a-tetramethylnaphtho[2,1-b]furan |
| 13851-11-1 | FENCHYL/ACETATE SUPER | 1,3,3-trimethyl-2-norbornanyl acetate |
| 80118-06-5 | ISO PENTYRATE | 1,3-Dimethyl-3-butenyl isobutyrate |
| 112-45-8 | UNDECYLENIC ALDEHYDE | 10-Undecenal |
| 53179-04-7 | FLORIDILE | 10-undecenenitrile |
| 112-30-1 | RHODALIONE | 1-Decanol |
| 2442-10-6 | AMYL VINYL CARBINYL ACETATE | 1-Octen-3-yl acetate |
| 106-02-5 | CYCLOPENTADECANOLIDE | 1-Oxacyclohexadecan-2-one |
| 128-51-8 | NOPYL ACETATE | 1R-(-)-Nopyl Acetate |
| 37172-02-4 | DIHYDRO AMBRATE | 2-(sec.Butyl)-1-vinylcyclohexyl acetate |
| 68039-49-6 | CYCLAL C | 2,4-Dimethyl-3-Cyclohexene-1-carboxaldehyde |
| 141-13-9 | ADOXAL | 2,6,10-Trimethyl-undec-9-enal |
| 13254-34-7 | DIMETHYL-2 6-HEPTAN-2-OL | 2,6-Dimethyl-2-heptanol |
| 7786-44-9 | 2,6-NONADIEN-1-OL | 2,6-Nonadien-1-ol |
| 23696-85-7 | DAMASCENONE | 2-Buten-1-one, 1-(2,6,6-trimethyl-1,3-cyclohexadien-1-yl)- |
| 28219-61-6 | DARTANOL | 2-Ethyl-4-(2,2,3-trimethylcyclopent-3-enyl-1)-2-buten-1-ol |
| 137-03-1 | FLEURAMONE | 2-Heptylcyclopentanone |
| 24168-70-5 | METHOXYISOBUTYLPYRAZINE @ 0.1% MPG FP246 | 2-Methoxy-3-(1-methylpropyl)pyrazine |
| 1205-17-0 | HELIONAL | 2-Methyl-3-(3,4-methylenedioxyphenyl)-propanal |
| 543-39-5 | MYRCENOL SUPER 13.2193 (CONF.-IFF) | 2-Methyl-6-methylene-7-octen-2-ol |
| 110-41-8 | METHYL NONYL ACETALDEHYDE | 2-Methylundecanal |
| 2463-53-8 | 2 NONEN-1-AL | 2-Nonen-1-al |
| 4819-67-4 | DELPHONE | 2-Pentylcyclopentanone |
| 103-60-6 | PHENOXY ETHYL ISO BUTYRATE | 2-Phenoxyethyl isobutyrate |
| 103-45-7 | PHENYL ETHYL ACETATE | 2-Phenylethyl acetate |
| 14765-30-1 | 2-SEC-BUTYL CYCLO HEXANONE | 2-sec.Butylcyclohexanone |
| 6784-13-0 | LIMINAL 955374 | 3-(4-Methylcyclohex-3-en-1-yl)-butyraldehyde |

-continued

| CAS | P&G Name | Chemical Name |
|---|---|---|
| 7775-00-0 | CYCLEMAX | 3-(p-Isopropylphenyl)propionaldehyde |
| 58430-94-7 | ISO NONYL ACETATE | 3,5,5-Trimethylhexyl acetate |
| 106-21-8 | DIMETHYL OCTANOL | 3,7-dimethyl-1-octanol |
| 67801-20-1 | EBANOL | 3-methyl-5-(2,2,3-trimethyl-3-cyclopenten-1-yl)pent-4-en-2-ol |
| 55066-49-4 | MEFRANAL | 3-Methyl-5-phenyl-1-pentanal |
| 20407-84-5 | ALDEHYDE MANDARINE 10% IN CITRATE | 3-Nonylacrolein |
| 18127-01-0 | BOURGEONAL | 4-(1,1-Dimethylethyl)benzenepropanal |
| 18096-62-3 | INDOFLOR CRIST. | 4,4a,5,9b-tetrahydroindeno[1,2-d]-1,3-dioxin |
| 13171-00-1 | MUSK INDANONE | 4-Acetyl-6-t-butyl-1,1-dimethylindane |
| 4621-04-9 | ROSELEA | 4-Isopropylcyclohexanol |
| 122-00-9 | PARA METHYL ACETOPHENONE | 4-Methylacetophenone |
| 562-74-3 | TERPINENOL-4 | 4-Terpinenol |
| 32210-23-4 | 4-TERTIARY BUTYL CYCLOHEXYL ACETATE | 4-tert.Butylcyclohexyl acetate |
| 16587-71-6 | ORIVONE | 4-tert-Amylcyclohexanone |
| 37609-25-9 | 5-CYCLOHEXADECEN-1-ONE | 5-Cyclohexadecenone |
| 22457-23-4 | STEMONE | 5-Methyl-3-heptanone oxime |
| 32764-98-0 | JASMOLACTONE | 6-(Z,3-Pentenyl)-tetrahydro-(2H)-pyranone-2 |
| 33885-51-7 | PINO ACETALDEHYDE | 6,6-dimethyl-2-norpinene-2-propionaldehyde |
| 70214-77-6 | NONADYL | 6,8-Diethyl-2-nonanol |
| 65442-31-1 | ISO BUTYL QUINOLINE | 6-isobutyl quinoline |
| 135-79-5 | ISOPROPYL QUINOLINE | 6-Isopropylquinoline |
| 91-62-3 | PARA METHYL QUINOLINE | 6-Methylquinoline |
| 1506-02-1 | AMTOLIDE | 7-Acetyl-1,1,3,4,4,6-hexamethyltetralin |
| 84697-09-6 | ACALEA TBHQ | Acalea |
| 100-06-1 | PARA METHOXY ACETOPH/BENZ/SALIC MX | Acetoanisole |
| 98-86-2 | ACETOPHENONE | Acetophenone |
| 67634-00-8 | ALLYL AMYL GLYCOLATE | Allyl amyl glycolate |
| 123-68-2 | ALLYL CAPROATE | Allyl caproate |
| 2705-87-5 | ALLYL CYCLOHEXANE PROPIONATE | Allyl cyclohexyl propionate |
| 142-19-8 | ALLYL HEPTANOATE 97+% FCC | Allyl heptanoate |
| 7493-74-5 | ALLYL PHENOXY ACETATE | Allyl phenoxyacetate |
| 67634-15-5 | FLORALOZONE | alpha,alpha-Dimethyl-p-ethylphenylpropanal |
| 122-40-7 | AMYL CINNAMIC ALDEHYDE | alpha-Amylcinnamaldehyde |
| 60763-41-9 | AMYL CINNAMIC ALDEHYDE DIETHYL ACETAL | alpha-Amylcinnamaldehyde diethyl acetal |
| 17627-44-0 | BISABOLENE | alpha-bisabolene |
| 24720-09-0 | ALPHA DAMASCONE | alpha-Damascone |
| 502-61-4 | BISABOLENE | alpha-Farnesene |
| 101-86-0 | HEXYL CINNAMIC ALDEHYDE | alpha-Hexylcinnamaldehyde |
| 127-41-3 | IONONE AB | alpha-Ionone |
| 79-69-6 | IRONE ALPHA REFINED | alpha-Irone |
| 127-51-5 | IONONE GAMMA METHYL | alpha-Isomethylionone |
| 98-55-5 | ALPHA TERPINEOL | alpha-Terpineol |
| 80-26-2 | LINDENYL-ACETATE | alpha-Terpinyl acetate |
| 2050-08-0 | AMYL SALICYLATE | amyl salicylate |
| 189440-77-5 | ANAPEAR 8753453 | Anapear |
| 104-21-2 | ANISYL ACETATE | Anisyl acetate |
| 25225-08-5 | APHERMATE | Aphermate |
| 89-43-0 | AURANTIOL | Aurantiol |
| 362467-67-2 | AZURONE 10 0015573 | Azurone |
| 100-52-7 | BENZALDEHYDE | Benzaldehyde |
| 119-61-9 | BENZOPHENONE | Benzophenone |
| 140-11-4 | BENZYL ACETATE | Benzyl acetate |
| 100-51-6 | BENZYL ALCOHOL | Benzyl alcohol |
| 120-51-4 | BENZYL BENZOATE | Benzyl benzoate |
| 103-37-7 | BENZYL BUTYRATE | Benzyl butyrate |
| 103-41-3 | BENZYL CINNAMATE | Benzyl cinnamate |
| 100-86-7 | DIMETHYL BENZYL CARBINOL | Benzyl dimethyl carbinol |
| 103-28-6 | BENZYL ISO BUTYRATE | Benzyl isobutyrate |
| 122-63-4 | BENZYL PROPIONATE | Benzyl propionate |
| 118-58-1 | BENZYL SALICYLATE | Benzyl salicylate |
| 2550-26-7 | BENZYL ACETONE | Benzylacetone |
| 103-05-9 | PHENYL ETHYL DIMETHYL CARBINOL | Benzyl-tert-butanol |
| 23267-57-4 | IONONE EPOXIDE, BETA | Beta ionone epoxide |
| 103-64-0 | BROM STYROL | beta-Bromstyrol |
| 87-44-5 | CARYOPHYLLENE EXTRA | beta-Caryophyllene |
| 23726-91-2 | DAMASCONE BETA | beta-Damascone (E-configuration) |

-continued

| CAS | P&G Name | Chemical Name |
|---|---|---|
| 18794-84-8 | BISABOLENE | beta-Farnesene |
| 185429-83-8 | GEORGYWOOD (CONF.-GIV) | beta-Georgywood |
| 14901-07-6 | BETA-IONONE 97+% FCC (CONF.-ALDRICH) | beta-Ionone |
| 123-35-3 | MYRCENE | beta-Myrcene |
| 127-91-3 | BETA PINENE | beta-Pinene |
| 72429-08-4 | BIGARADE OXIDE | Bigarade oxide |
| 495-62-5 | BISABOLENE | Bisabolene |
| 58567-11-6 | BOISAMBRENE FORTE (S 506) | Boisambrene forte |
| 24717-86-0 | ABIERATE CN (C SYN) | Bornyl isobutyrate |
| 3155-71-3 | BORONAL | Boronal |
| 72089-08-8 | BRAHMANOL F/3/071130 | Brahmanol |
| 75147-23-8 | BUCCOXIME | Buccoxime |
| 136-60-7 | BUTYL BENZOATE | Butyl benzoate |
| 128-37-0 | BUTYLATED HYDROXY TOLUENE | Butylated hydroxytoluene |
| 79-92-5 | CAMPHENE | Camphene |
| 76-22-2 | CAMPHOR GUM | Camphor |
| 5462-06-6 | CANTHOXAL (03-0952) | Canthoxal |
| 112-31-2 | DECYL ALDEHYDE | Capraldehyde |
| 111-87-5 | OCTYL ALCOHOL | Caprylic alcohol |
| 124-13-0 | OCTYL ALDEHYDE | Caprylic aldehyde |
| 33704-61-9 | CASHMERAN | Cashmeran |
| 77-53-2 | CEDROL | Cedrol |
| 77-54-3 | CEDAC | cedryl acetate |
| 19870-74-7 | CEDRYL METHYL ETHER | Cedryl methyl ether |
| 3720-16-9 | LIVESCONE | Celery ketone |
| 6707-60-4 | 12 OXAHEXADECECANOLIDE | Cervolide |
| 79-78-7 | HEXALON | Cetone V |
| 88-04-0 | 4-CHLORO 3,5 XYLENOL | Chloroxylenol |
| 1885-38-7 | CINNAMALVA | Cinamalva |
| 104-54-1 | CINNAMIC ALCOHOL | Cinnamic alcohol |
| 104-55-2 | CINNAMIC ALDEHYDE | Cinnamic aldehyde |
| 103-54-8 | CINNAMYL ACETATE | Cinnamyl acetate |
| 53046-97-2 | 3,6-N0NADIEN-1-OL | cis-3, cis-6-nonadienol |
| 928-96-1 | BETA GAMMA HEXENOL | cis-3-Hexen-1-ol |
| 53398-85-9 | CIS-3-HEXENYL ALPHA METHYL BUTYRATE | cis-3-Hexenyl 2-methylbutyrate |
| 3681-71-8 | CIS 3 HEXENYL ACETATE | cis-3-Hexenyl acetate |
| 25152-85-6 | CIS-3-HEXENYL BENZOATE | Cis-3-hexenyl Benzoate |
| 16491-36-4 | CIS 3 HEXENYL BUTYRATE | cis-3-Hexenyl butyrate |
| 65405-77-8 | CIS-3-HEXENYL SALICYLATE | cis-3-Hexenyl salicylate |
| 67883-79-8 | CIS-3-HEXENYL TIGLATE | cis-3-Hexenyl tiglate |
| 36508-31-3 | CIS-ISO-AMBRETTOLIDE | Cis-iso-ambrettolide |
| 488-10-8 | CIS JASMONE | cis-Jasmone |
| 5392-40-5 | CITRAL | Citral |
| 7549-37-3 | CITRAL DIMETHYL ACETAL | Citral dimethyl acetal |
| 106-23-0 | CITRONELLAL | Citronellal |
| 106-22-9 | CITRONELLOL | Citronellol |
| 150-84-5 | CITRONELLYL ACETATE | Citronellyl acetate |
| 105-85-1 | CITRONELLYL FORMATE | Citronellyl formate |
| 51566-62-2 | BARANYL NITRILE | Citronellyl nitrile |
| 141-14-0 | CITRONELLYL PROPIONATE | Citronellyl propionate |
| 7492-67-3 | CITRONELLYL OXYACETALDEHYDE | Citronellyloxyacetaldehyde |
| 97384-48-0 | CITROWANIL B | Citrowanil B |
| 6819-19-8 | CITRYL ACETATE | Citryl acetate |
| 83926-73-2 | CORANOL (CONF.-FIRM) | Coranol |
| 91-64-5 | COUMARIN | Coumarin |
| 122-03-2 | CUMINIC ALDEHYDE | Cuminaldehyde |
| 13816-33-6 | CUMIN NITRILE | Cuminyl nitrile |
| 67634-20-2 | CYCLABUTE | Cyclabute |
| 103-95-7 | CYMAL | Cyclamen aldehyde |
| 68991-97-9 | MELAFLEUR MO9962 | Cyclemone A |
| 54982-83-1 | ZENOLIDE | Cyclic ethylene dodecanedioate |
| 113889-23-9 | CYCLOBUTANATE 081145 | cyclobutanate |
| 68901-15-5 | CYCLO GALBANATE | Cyclogalbanate |
| 22471-55-2 | THESARON | Cyclohexanecarboxylic acid, 2,2,6-trimethyl-, ethyl ester, (1R,6S)-rel- |
| 25485-88-5 | CYCLOHEXYL SALICYLATE | Cyclohexyl salicylate |
| 21722-83-8 | CYCLOHEXYL ETHYL ACETATE | Cyclohexylethyl acetate |
| 84560-00-9 | CYCLOPENTOL | Cyclopentol |
| 40203-73-4 | CYCLOPIDENE 937160 | Cyclopentylideneacetic acid, methyl ester |
| 68039-69-0 | DATILAT | Datilat |
| 5454-19-3 | N-DECYL PROPIONATE | Decyl propionate |
| 13019-22-2 | ROSALVA | Decylenic alcohol |

-continued

| CAS | P&G Name | Chemical Name |
|---|---|---|
| 57378-68-4 | DELTA DAMASCONE | delta-damascone |
| 705-86-2 | DECALACTONE | delta-Decalactone |
| 82356-51-2 | DELTA MUSCENONE 962191 | Delta-Muscenone |
| 431-03-8 | DIACETYL 0.1% IN DPG | Diacetyl |
| 105-53-3 | DIETHYL MALONATE | Diethyl malonate |
| 84-66-2 | DIETHYLPHTHALATE | Diethyl phthalate |
| 37172-53-5 | DIHYDRO ISO JASMONATE | Dihydro Isojasmonate |
| 498-81-7 | DIHYDROTERPINEOL | Dihydro Terpineol |
| 17283-81-7 | DIHYDRO BETA IONONE | Dihydro-beta-ionone |
| 119-84-6 | DIHYDROCOUMARIN | Dihydrocoumarin |
| 64001-15-6 | DIHYDRO CYCLACET | Dihydrocyclacet |
| 2785-87-7 | DIHYDRO EUGENOL | Dihydroeugenol |
| 1128-08-1 | DIHYDROJASMONE | Dihydrojasmone |
| 18479-58-8 | DIMYRCETOL | Dihydromyrcenol |
| 80-25-1 | MENTHANYL ACETATE | Dihydroterpinyl acetate |
| 85-91-6 | DIMETHYL ANTHRANILATE | Dimethyl anthranilate |
| 151-05-3 | DIMETHYL BENZYL CARBINYL ACETATE | Dimethyl benzyl carbinyl acetate |
| 10094-34-5 | DIMETHYL BENZYL CARBINYL BUTYRATE | Dimethyl benzyl carbinyl butyrate |
| 103-05-9 | PHENYL ETHYL DIMETHYL CARBINOL | dimethyl phenyl ethyl carbinol |
| 138-86-3 | DIPENTENE | Dipentene |
| 101-81-5 | DIPHENYL METHANE | Diphenylmethane |
| 101-84-8 | DIPHENYL OXIDE | Diphenyloxide |
| 25265-71-8 | ABSOLUTE VANILLA 50 DPG 99FP/1133(C-FR) | Dipropylene Glycol |
| 89-48-5 | MENTHYL ACETATE 620020 | dl-Menthyl acetate |
| 2556-10-7 | HYACINTH BODY 08-8735 | Efetaal |
| 40910-49-4 | ELINTAAL FORTE | Elintaal |
| 140-67-0 | ESTRAGOL EX BADIANE | Estragole |
| 6413-10-1 | 690965 JASMAPRUNAT | Ethyl 2-methyl-1,3-dioxolane-2-acetate |
| 7452-79-1 | ETHYL-2-METHYL BUTYRATE | Ethyl 2-methylbutyrate |
| 101-97-3 | ETHYL PHENYL ACETATE | Ethyl 2-phenylacetate |
| 5405-41-4 | ETHYL-3-HYDROXY BUTYRATE | Ethyl 3-hydroxybutyrate |
| 121-39-1 | ETHYL PHENYL GLYCIDATE | Ethyl 3-phenylglycidate |
| 141-78-6 | ETHYL ACETATE | Ethyl acetate |
| 141-97-9 | ETHYL ACETOACETATE | Ethyl acetoacetate |
| 589-98-0 | OCTANOL-3 | Ethyl amyl carbinol |
| 106-68-3 | ETHYL AMYL KETONE | Ethyl amyl ketone |
| 35044-59-8 | ETHYL SAFRANATE | Ethyl beta-safranate |
| 105-54-4 | ETHYL BUTYRATE | Ethyl butanoate |
| 103-36-6 | ETHYL CINNAMATE | Ethyl cinnamate |
| 106-30-9 | ETHYL OENANTHATE | Ethyl heptoate |
| 123-66-0 | ETHYL CAPROATE FCC (GIVAUDAN) | Ethyl hexanoate |
| 925-78-0 | ETHYL HEXYL KETONE | Ethyl hexyl ketone |
| 10339-55-6 | ETHYL LINALOOL | Ethyl linalool |
| 4940-11-8 | ETHYL MALTOL | Ethyl Maltol |
| 77-83-8 | ETHYL METHYL PHENYL GLYCIDATE | Ethyl methylphenylglycidate |
| 105-37-3 | ETHYL PROPIONATE | Ethyl propionate |
| 118-61-6 | ETHYL SALICYLATE | Ethyl salicylate |
| 3025-30-7 | ETHYL 2,4-DECADIENOATE | Ethyl trans-2,cis-4-decadienoate |
| 121-32-4 | ETHYL VANILLIN | Ethyl vanillin |
| 105-95-3 | ETHYLENE BRASSYLATE | Ethylene brassylate |
| 470-82-6 | EUCALYPTOL | Eucalyptol |
| 97-53-0 | EUGENOL | Eugenol |
| 14595-54-1 | EXALTENONE 942008 | Exaltenone |
| 4602-84-0 | FARNESOL | Farnesol |
| 1632-73-1 | FENCHYL ALCOHOL | Fenchyl alcohol |
| 81925-81-7 | FILBERTONE 1% IN TEC 736664 | Filbertone G |
| 134123-93-6 | FLEURANIL | Fleuranil |
| 67634-26-8 | FLORALATE 062960 | Floralate |
| 67634-25-7 | FLORALATE 062960 | Floralate |
| 125109-85-5 | FLORHYDRAL | Florhydral |
| 63500-71-0 | FLOROL | Florosa Q |
| 80657-64-3 | FRUITATE | Fruitate |
| 35206-51-0 | FRUTINAT 611 400 | Frutinat |
| 69300-15-8 | FRUTONILE | Frutonile |
| 1222-05-5 | GALAXOLIDE 50% CITROFLEX (C IFF) | Galaxolide |
| 35087-49-1 | GAMMA DAMASCONE 944580 | gamma-Damascone |
| 706-14-9 | GAMMA DECALACTONE | gamma-Decalactone |
| 2305-05-7 | DODECALACTONE | gamma-Dodecalactone |
| 695-06-7 | GAMMA HEXALACTONE | gamma-Hexalactone |
| 104-61-0 | NONALACTONE | gamma-Nonalactone |

-continued

| CAS | P&G Name | Chemical Name |
|---|---|---|
| 104-50-7 | GAMMA OCTALACTONE FCC | gamma-Octalactone |
| 104-67-6 | PEACH ALDEHYDE COEUR | gamma-Undecalactone (racemic) |
| 105-87-3 | GERANYL ACETATE | Geranyl acetate |
| 106-29-6 | GERANYL BUTYRATE | Geranyl butyrate |
| 68133-79-9 | APRITONE | Geranyl cyclopentanone |
| 105-86-2 | GERANYL FORMATE | Geranyl formate |
| 5146-66-7 | CITRALVA PLUS | Geranyl nitrile |
| 102-22-7 | GERANYL PHENYLACETATE | Geranyl phenylacetate |
| 57934-97-1 | GIVESCONE | Givescone |
| 68901-32-6 | GLYCOLIERRAL | Glycolierral |
| 68611-23-4 | GRISALVA | Grisalva |
| 24237-00-1 | GYRANE | Gyrane |
| 34902-57-3 | HABANOLIDE 100% | Habanolide |
| 120-57-0 | HELIOTROPIN | Heliotropin |
| 40527-42-2 | HELIOTROPIN DIETHYL ACETAL | Heliotropine diethyl acetal |
| 141773-73-1 | HELVETOLIDE 947650 | Helvetolide |
| 25304-14-7 | HERBAC | Herbac |
| 116044-44-1 | HERBANATE | Herbanate |
| 54546-26-8 | HERBOXANE | Herboxane |
| 109-29-5 | SILVANONE CI | Hexadecanolide |
| 3681-73-0 | HEXAROSE 947855 | Hexarose |
| 10032-15-2 | HEXYL-2-METHYL BUTYRATE | Hexyl 2-methylbutanoate |
| 142-92-7 | HEXYL ACETATE | Hexyl acetate |
| 2349-07-7 | HEXYL ISOBUTYRATE | Hexyl isobutyrate |
| 111-13-7 | METHYL HEXYL KETONE | Hexyl methyl ketone |
| 93-53-8 | HYDRATROPIC ALDEHYDE LA | Hydratropaldehyde |
| 122-97-4 | PHENYL PROPYL ALCOHOL | Hydrocinnamyl alcohol |
| 118562-73-5 | HYDROXYAMBRAN | Hydroxyambran |
| 107-75-5 | HYDROXYCITRONELLAL | Hydroxycitronellal |
| 107-74-4 | HYDROXYOL | Hydroxy-citronellol |
| 120-72-9 | INDOL | Indole |
| 28645-51-4 | AMBRETTOLIDE | Isoambrettolide |
| 123-92-2 | AMYL-ACETATE (ISOMER BLENDS) | Isoamyl acetate |
| 68683-20-5 | ISO BERGAMATE | Isobergamate |
| 125-12-2 | ISO BORNYL ACETATE | Isobornyl acetate |
| 66072-32-0 | ISO BORNYL CYCLOHEXANOL | Isobornyl cyclohexanol |
| 2756-56-1 | ISO BORNYL PROPIONATE | Isobornyl propionate |
| 110-19-0 | NATURAL ISOBUTYL ACETATE | Isobutyl acetate |
| 105-79-3 | ISO BUTYL CAPROATE | Isobutyl caproate |
| 102-13-6 | ISO BUTYL PHENYLACETATE | Isobutyl phenylacetate |
| 87-19-4 | ISO BUTYL SALICYLATE | Isobutyl salicylate |
| 1335-66-6 | ISO CYCLO CITRAL | Isocyclocitral |
| 68527-77-5 | ISOCYCLOGERANIOL | Isocyclogeraniol |
| 39872-57-6 | ISODAMASCONE N 3/055152 | Isodamascone |
| 54464-57-2 | ISO CYCLEMONE E | Iso-E Super |
| 97-54-1 | ISO EUGENOL | Isoeugenol |
| 93-29-8 | ISO EUGENOL ACETATE | Isoeugenyl acetate |
| 120-11-6 | BENZYL ISO EUGENOL | Isoeugenyl benzyl ether |
| 37677-14-8 | ISO HEXENYL CYCLOHEXENYL CARBOXALDEHYDE | Isohexenyl cyclohexenyl carboxaldehyde |
| 95-41-0 | ISO JASMONE | Isojasmone |
| 491-07-6 | ISO MENTHONE | Isomenthone |
| 123-51-3 | ISOAMYL ALCOHOL, 98+% | Isopentanol |
| 106-27-4 | AMYL BUTYRATE | Isopentyl butyrate; |
| 66576-71-4 | ISO PROPYL 2-METHYLBUTYRATE | Isopropyl 2-methylbutyrate |
| 110-27-0 | GALAXOLIDE 50 IPM | Isopropyl myristate |
| 89-79-2 | ISO PULEGOL | Isopulegol |
| 18871-14-2 | DIASMOL | Jasmal |
| 208041-98-9 | JASMONITRILE 952906 | jasmonitrile |
| 198404-98-7 | JAVANOL (CONF.-GIV) | Javanol |
| 36306-87-3 | LRG 182 | Kephalis |
| 75490-39-0 | KHUSINIL | Khusinil |
| 86115-11-9 | KOAVONE | Koavone |
| 92015-65-1 | KOUMALACTONE 953320 | Koumalactone |
| 112-54-9 | LAURIC ALDEHYDE | Lauraldehyde |
| 2437-25-4 | ALDINYLE 3881 (CONF.-SYN) | Lauronitrile |
| 6485-40-1 | LAEVO CARVONE | L-Carvone |
| 67633-96-9 | LIFFAROME | Liffarome |
| 80-54-6 | P.T.BUCINAL | Lilial |
| 7392-19-0 | LRG 188 | Limetol |
| 61792-11-8 | LEMONILE | Limonile |
| 78-70-6 | LINALOOL | Linalool |
| 115-95-7 | LINALYL ACETATE | Linalyl acetate |
| 126-64-7 | LINALYL BENZOATE | Linalyl benzoate |
| 115-99-1 | LINALYL FORMATE | Linalyl formate |

-continued

| CAS | P&G Name | Chemical Name |
|---|---|---|
| 115-99-1 | LINALYL FORMATE | Linalyl formate |
| 78-35-3 | LINALYL ISO BUTYRATE | Linalyl isobutyrate |
| 144-39-8 | LINALYL PROPIONATE | Linalyl propionate |
| 31906-04-4 | LYRAL | Lyral |
| 67845-30-1 | MACEAL | Maceal |
| 103694-68-4 | MAJANTOL | Majantol |
| 118-71-8 | MALTOL | Maltol |
| 134769-33-8 | MANDARIL 600 135 | Mandaril |
| 13828-37-0 | MAYOL | Mayol |
| 106-72-9 | MELONAL | Melonal |
| 30772-79-3 | FORMYLTRICYCLODECAN | Melozone |
| 89-80-5 | MENTHONE RACEMIC | Menthone |
| 3613-30-7 | METHOXYCITRONELLAL PQ | Methoxycitronellal |
| 62439-41-2 | METHOXY MELONAL | Methoxymelonal |
| 111-80-8 | METHYL OCTINE CARBONATE | Methyl 2-nonynoate |
| 111-12-6 | METHYL HEPTINE CARBONATE | Methyl 2-octynoate |
| 28043-10-9 | METHYL CYCLOGERANATE | Methyl a-cyclogeranate |
| 134-20-3 | METHYL ANTHRANILATE | Methyl anthranilate |
| 91-51-0 | P.T. BUCINAL METHYL ANTHRANILATE | Methyl anthranilate/lilial Schiff base |
| 93-58-3 | METHYL BENZOATE | Methyl benzoate |
| 93-08-3 | METHYL BETA-NAPHTHYL KETONE | Methyl beta-naphthyl ketone |
| 103-26-4 | METHYL CINNAMATE | Methyl cinnamate |
| 24851-98-7 | HEDIONE HC | Methyl dihydrojasmonate |
| 93-15-2 | METHYL EUGENOL | Methyl eugenol |
| 93-16-3 | METHYL ISO EUGENOL | Methyl isoeugenol |
| 67633-95-8 | METHYL LAVENDER KETONE | Methyl lavender ketone |
| 68141-17-3 | METHYL NONYL ACETALDEHYDE DIMETHYL ACETA | Methyl nonyl acetaldehyde dimethyl acetal |
| 112-12-9 | METHYL NONYL KETONE | Methyl nonyl ketone |
| 39212-23-2 | METHYL OCTALACTONE | Methyl Octalactone |
| 19009-56-4 | METHYL OCTYL ACETALDEHYDE | Methyl octyl acetaldehyde |
| 67674-46-8 | METHYL PAMPLEMOUSSE | Methyl Pamplemousse |
| 110-43-0 | METHYL AMYL KETONE | Methyl pentyl ketone |
| 3558-60-9 | KEONE | Methyl phenethyl ether |
| 93-92-5 | METHYL PHENYL CARBINYL ACETATE | Methyl Phenyl Carbinyl Acetate |
| 101-41-7 | METHYL PHENYL ACETATE | Methyl phenylacetate |
| 119-36-8 | METHYL SALICYLATE USP | Methyl salicylate |
| 188570-78-7 | MONTAVERDI | Montaverdi |
| 18479-54-4 | MUGUOL | Muguol |
| 541-91-3 | LAEVO MUSCONE | Muscone |
| 1118-39-4 | PSEUDO LINALYL ACETATE | Myrcenyl acetate |
| 95962-14-4 | NECTALACTONE DSR 95430109 | Nectaryl |
| 56973-85-4 | GALBASCONE | Neobutenone |
| 111-79-5 | METHYL-2-NONENOATE | Neofolione |
| 106-25-2 | NEROL | Nerol |
| 7212-44-4 | NEROLIDOL | Nerolidol |
| 93-04-9 | BETA NAPHTHOL METHYL ETHER | Nerolin |
| 23911-56-0 | NEROLIONE 600321 | Nerolione |
| 141-12-8 | NERYL ACETATE | Neryl acetate |
| 66-25-1 | HEXYL ALDEHYDE | n-Hexanal |
| 6259-76-3 | HEXYL SALICYLATE | n-Hexyl salicylate |
| 124-19-6 | NONYL ALDEHYDE | Nonaldehyde |
| 143-08-8 | NONYL ALCOHOL | Nonyl alcohol |
| 128-51-8 | NOPYL ACETATE | Nopyl acetate |
| 5986-38-9 | OCIMENOL | Ocimenol |
| 30168-23-1 | DUPICAL | Octahydro-4,7-methanoindanilydenebutanal |
| 86803-90-9 | SCENTENAL | octahydro-5-methoxy-4,7-Methano-1H-indene-2-carboxaldehyde |
| 4430-31-3 | BICYCLONONALACTONE | Octahydrocoumarin |
| 103614-86-4 | OCTALYNOL (CONF.-FIRM) | Octalynol |
| 131812-67-4 | OKOUMAL | Okoumal |
| 88-41-5 | 2-T-BUTYL CYCLOHEXYL ACETATE | o-tert-Butylcyclohexyl acetate |
| 1725-01-5 | OXALIDE T | Oxalide |
| 28940-11-6 | CALONE 1951 | Oxalone |
| 59323-76-1 | OXANE | Oxane |
| 22629-49-8 | 2-TRIDECENENITRILE | Ozonil |
| 123-11-5 | ANISIC ALDEHYDE | p-Anisaldehyde |
| 5471-51-2 | PARA HYDROXY PHENYL BUTANONE | para-hydroxy phenyl butanone |
| 142653-61-0 | PARMANYL 3/055119 | Parmanyl |

-continued

| CAS | P&G Name | Chemical Name |
|---|---|---|
| 98-52-2 | PATCHON | Patchone |
| 5986-55-0 | HEALINGWOOD | Patchouli alcohol |
| 106-44-5 | PARA CRESOL | p-Cresol |
| 103-93-5 | PARA CRESYL ISO BUTYRATE | p-Cresyl isobutyrate |
| 104-93-8 | PARA CRESYL METHYL ETHER | p-Cresyl methyl ether |
| 99-87-6 | CYMENE COEUR | p-Cymene |
| 67663-01-8 | PEACHOLIDE 600038 | Peacholide |
| 39255-32-8 | ETHYL 2 METHYL PENTANOATE | Pentanoic acid, 2-methyl-, ethyl ester |
| 10461-98-0 | PEONILE | Peonile |
| 313973-37-4 | PHARAONE 10 | Pharaone |
| 80858-47-5 | PHENAFLEUR | Phenafleur |
| 60-12-8 | PHENYL ETHYL ALCOHOL | Phenethyl alcohol |
| 104-62-1 | PHENYL ETHYL FORMATE | Phenethyl formate |
| 56011-02-0 | PHENYL ETHYL ISOAMYL ETHER (AKA ANTHER) | Phenethyl isoamyl ether |
| 103-48-0 | PHENYL ETHYL ISO BUTYRATE | Phenethyl isobutyrate |
| 102-20-5 | PHENYL ETHYL PHENYL ACETATE | Phenethyl phenylacetate |
| 55066-48-3 | PHENOXANOL | Phenoxanol |
| 23495-12-7 | PHENOXL ETHYL PROPIONATE | Phenoxyethyl propionate |
| 122-78-1 | PHENYL ACETALDEHYDE | Phenylacetaldehyde |
| 101-48-4 | PHENYL ACETALDEHYDE DIMETHYL ACETAL | Phenylacetaldehyde dimethyl acetal |
| 5331-14-6 | CRESSANTHER | Phenylethyl n-butyl ether |
| 55418-52-5 | DULCINYL RECRYSTALIZED | Piperonyl acetone |
| 67662-96-8 | PIVAROSE | Pivarose Q |
| 41724-19-0 | PLICATONE | Plicatone |
| 107898-54-4 | NIRVANOL 974650 | Polysantol |
| 358331-95-0 | POMAROSE | Pomarose |
| 104-45-0 | DIHYDROANETHOLE, FCC- | p-Propyl anisole |
| 52474-60-9 | PRECYCLEMONE B | Precyclemone B |
| 1191-16-8 | PRENYL ACETATE | Prenyl acetate |
| 68555-58-8 | PRENYL SALICYLATE | Prenyl salicylate |
| 98-54-4 | PARA TERTIARY BUTYL PHENOL | p-tert-Butylphenol |
| 101-94-0 | PARA CRESYL PHENYL ACETATE | p-Tolyl phenylacetate |
| 80-56-8 | ALPHA PINENE | Racemic alpha-Pinene |
| 141-25-3 | RHODINOL 70 | Rhodinol |
| 82461-14-1 | RHUBAFURAN | Rhubafuran |
| 236391-76-7 | ROMANDOLIDE 979031 | Romanolide |
| 81752-87-6 | ROMASCONE | Romascone |
| 25225-10-9 | ROSAMUSK | Rosamusk |
| 16409-43-1 | METHYL ISO BUTENYL TETRAHYDRO PYRAN | Rose oxide |
| 215231-33-7 | ROSSITOL | Rossitol |
| 65113-99-7 | SANDALORE | Sandalore |
| 224031-70-3 | SPIROGALBANONE 10 | Spirogalbanone |
| 22457-23-4 | STEMONE | Stemone |
| 13215-88-8 | TABANON COEUR 659672 | Tabanone |
| 8000-41-7 | ALPHA TERPINEOL | Terpineol |
| 586-62-9 | TERPINEOLENE | Terpinolene |
| 5988-91-0 | DIHYDROCITRONELLAL | Tetrahydrogeranial |
| 13074-63-0 | JASMYLONE | Tetrahydrojasmone |
| 78-69-3 | LINACSOL | Tetrahydrolinalool |
| 20780-48-7 | TETRAHYDRO LINAYL ACETATE | Tetrahydrolinalyl acetate |
| 18479-57-7 | TETRA HYDRO MUGUOL | Tetrahydromyrcenol |
| 89-83-8 | THYMOL NF | Thymol |
| 3913-81-3 | 2 DECENE-1-AL | trans-2-Decenal |
| 928-95-0 | TRANS-2-HEXENOL | trans-2-Hexenol |
| 65405-70-1 | DECENAL (TRANS-4) | trans-4-Decen-1-al |
| 4180-23-8 | ANETHOL USP | trans-Anethole |
| 106-24-1 | ALGUE NE | trans-Geraniol |
| 90-17-5 | TRICHLOROMETHYL PHENYL CARBINYL ACETATE | Trichloromethyl phenyl carbinyl acetate |
| 2500-83-6 | FLOR ACETATE | Tricyclodecenyl acetate/Flor Acetate |
| 77-93-0 | GALBANOLENE SUPER 10% IN TEC | Triethyl citrate |
| 16251-77-7 | TRIFERNAL 989-007 | Trifernal |
| 112-44-7 | UNDECYL ALDEHYDE | Undecanal |
| 81782-77-6 | UNDECAVERTOL | Undecavertol |
| 121-33-5 | VANILLIN | Vanillin |
| 20665-85-4 | ISO BUTAVAN | Vanillin isobutyrate |
| 94-86-0 | VANITROPE | Vanitrope |
| 5533-03-9 | VANIWHITE | Vaniwhite |
| 65443-14-3 | VELOUTONE | veloutone |

-continued

| CAS | P&G Name | Chemical Name |
|---|---|---|
| 4707-47-5 | LRG 201 | Veramoss |
| 120-14-9 | CORPS 4322 | Veratraldehyde |
| 27135-90-6 | VERDALIA A | Verdalia A |
| 13491-79-7 | VERDOL | Verdol |
| 41519-23-7 | VERDURAL B EXTRA | Verdural B Extra |
| 32388-55-9 | ACETYL CEDRENE | Vertofix |
| 68738-99-8 | AGRUMEA | Vertosine |
| 68083-58-9 | VETIKOL ACETATE 3/080515 | Vetikol acetate |
| 87731-18-8 | VIOLIFF | Violiff |
| 133636-82-5 | WOLFWOOD 992393 | Wolfwood |
| 154171-76-3 | YSAMBER K 3/055120 | Ysamber |
| 105-68-0 | AMYL PROPIONATE | |
| 93-99-2 | PHENYL BENZOATE | |
| 94-47-3 | PHENYL ETHYL BENZOATE | |

In one aspect, the flavor may comprise a flavor used in oral care-type compositions, and may comprise Menthol (L, D, racemic), anethole and anise oil, eucalyptol and eucalyptus oil, peppermint oils, cornmint or arvensis mint oils, spearmint oils, 1 carvone, clove oils, cinnamic aldehyde and cinnamon derivatives, cooling agents (also referred to as sensates, such as those described in USPA 2007/0233026 A1) such as aliphatic carboxamides (including WS-3 available as ISE 3000 from Qaroma, Inc. and WS-23 available as ISE 1000 from Qaroma, Inc.), ketals (including MGA (available from Symrise)), cyclohexyl derivatives (including TK10, Coolact available from LIPO Chemicals of Paterson, N.J.), and monomenthyl succinated (available under the tradename Physcool), sweeteners such as sodium saccharin, sucralose, neohesperidine, eugenol and clove oils, cinnamic aldehyde and cinnamon derivatives, spicy flavor materials, methyl salicylate and wintergreen derivatives, and combinations thereof.

In one aspect, the flavor may comprise a flavor 'modifier,' and may include a fruity or dairy flavor such as vanillin, ethyl vanillin, sulphur derivatives for dairy notes and or exotic fruits, furan one, ethyl esters, damascones, ionones, allyl esters, butyric esters, essential oils of flowers, leaves and wood, absolutes, extracts of plants, and combinations thereof.

Useful perfume raw materials, accords and flavors may be obtained from one or more of the following companies Firmenich (Geneva, Switzerland), Givaudan (Argenteuil, France), IFF (Hazlet, N.J.), Quest (Mount Olive, N.J.), Bedoukian (Danbury, Conn.), Sigma Aldrich (St. Louis, Mo.), Millennium Specialty Chemicals (Olympia Fields, Ill.), Polarone International (Jersey City, N.J.), Fragrance Resources (Keyport, N.J.), and Aroma & Flavor Specialties (Danbury, Conn.).

Process of Making Encapsulated Benefit Agents

The encapsulated benefit agents employed herein may be made via the teachings of U.S. Pat. Nos. 6,592,990 B2 and/or 6,544,926 B1 and the examples disclosed herein.

Anionic emulsifiers are typically used during the encapsulation process to emulsify the benefit agent prior to microcapsule formation. While not being bound by theory, it is believed that the anionic materials adversely interact with the cationic surfactant actives that are often found in compositions such as fabric care compositions—this may yield an aesthetically unpleasing aggregation of particles that are employed in said composition. In addition to the unacceptable aesthetics, such aggregates may result in rapid phase separation of the particles from the bulk phase. Applicants discovered that such aggregates can be prevented by the addition of certain aggregate inhibiting materials including materials selected from the group consisting of salts, polymers and mixtures thereof. Useful aggregate inhibiting materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride n-hydrate and polymers that have the ability to suspend anionic particles such as soil suspension polymers, for example, (polyethylene imines, alkoxylated polyethylene imines, polyquaternium-6 and polyquaternium-7.

In one aspect of the invention, encapsulated benefit agents are manufactured and are subsequently coated with a material to reduce the rate of leakage of the benefit agent from the particles when the particles are subjected to a bulk environment containing, for example, surfactants, polymers, and solvents. Non-limiting examples of coating materials that can serve as barrier materials include materials selected from the group consisting of polyvinyl pyrrolidone homopolymer, and its various copolymers with styrene, vinyl acetate, imidazole, primary and secondary amine containing monomers, methyl acrylate, polyvinyl acetal, maleic anhydride; polyvinyl alcohol homopolymer, and its various copolymers with vinyl acetate, 2-acrylamide-2-methylpropane sulfonate, primary and secondary amine containing monomers, imidazoles, methyl acrylate; polyacrylamides; polyacrylic acids; microcrystalline waxes; paraffin waxes; modified polysaccharides such as waxy maize or dent corn starch, octenyl succinated starches, derivatized starches such as hydroxyethylated or hydroxypropylated starches, carrageenan, guar gum, pectin, xanthan gum; modified celluloses such as hydrolyzed cellulose acetate, hydroxy propyl cellulose, methyl cellulose, and the like; modified proteins such as gelatin; hydrogenated and non-hydrogenated polyalkenes; fatty acids; hardened shells such as urea crosslinked with formaldehyde, gelatin-polyphosphate, melamine-formaldehyde, polyvinyl alcohol crosslinked with sodium tetraborate or gluteraldehyde; latexes of styrene-butadiene, ethyl cellulose, inorganic materials such as clays including magnesium silicates, aluminosilicates; sodium silicates, and the like; and mixtures thereof. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey U.S.A.

Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., USA), Arde Barinco (New Jersey, USA).

Formaldehyde Scavenging

In one aspect, encapsulated benefit agent may be combined with a formaldehyde scavenger. In one aspect, encapsulated benefit agent may comprise the encapsulated benefit agent of the present invention. Suitable formaldehyde scavengers include materials selected from the group consisting of sodium bisulfite, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or PolySciences, Inc. of Warrington, Pa. U.S.A.

Such formaldehyde scavengers are typically combined with a slurry containing said benefit agent containing delivery particle, at a level, based on total slurry weight, of from about 2 wt. % to about 18 wt. %, from about 3.5 wt. % to about 14 wt. % or even from about 5 wt. % to about 13 wt. %.

In one aspect, such formaldehyde scavengers may be combined with a product containing a benefit agent containing delivery particle, said scavengers being combined with said product at a level, based on total product weight, of from about 0.005% to about 0.8%, alternatively from about 0.03% to about 0.5%, alternatively from about 0.065% to about 0.25% of the product formulation.

In another aspect, such formaldehyde scavengers may be combined with a slurry containing said encapsulated benefit agent, at a level, based on total slurry weight, of from about 2 wt. % to about 14 wt. %, from about 3.5 wt. % to about 14 wt. % or even from about 5 wt. % to about 14 wt. % and said slurry may be added to a product matrix to which addition an identical or different scavenger may be added at a level, based on total product weight, of from about 0.005% to about 0.5%, alternatively from about 0.01% to about 0.25%, alternatively from about 0.05% to about 0.15% of the product formulation, In one aspect, one or more of the aforementioned formaldehyde scavengers may be combined with a consumer product containing an encapsulated benefit agent at a level, based on total liquid fabric enhancing product weight, of from 0.005% to about 0.8%, alternatively from about 0.03% to about 0.4%, alternatively from about 0.06% to about 0.25% of the product formulation In one aspect, such formaldehyde scavengers may be combined with a liquid laundry detergent product containing a benefit agent containing delivery particle, said scavengers being selected from the group consisting of sodium bisulfite, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid and mixtures thereof, and combined with said liquid laundry detergent product at a level, based on total liquid laundry detergent product weight, of from about 0.003 wt. % to about 0.20 wt. %, or from about 0.03 wt. % to about 0.20 wt. % or from about 0.06 wt. % to about 0.14 wt. %.

In one aspect, such formaldehyde scavengers may be combined with a hair conditioning product containing a benefit agent containing delivery particle, at a level, based on total hair conditioning product weight, of from about 0.003 wt. % to about 0.30 wt. %, from about 0.03 wt. % to about 0.20 wt. % or from about 0.06 wt. % to about 0.14 wt. %, said selection of scavengers being identical to the list of scavengers in the previous paragraph relating to a liquid laundry detergent product.

Compositions Comprising Benefit Agent Containing Delivery Particles

Applicants' consumer products may comprise an embodiment of the benefit agent delivery composition disclosed in the present application. In one aspect, said consumer products may be a powdered, granule or other essentially dry detergent.

In one aspect, a consumer product that may comprise one or more of the benefit agent delivery compositions of the present invention and an adjunct ingredient is disclosed.

In one aspect of the aforementioned consumer product, said consumer product adjunct may be selected from the group consisting of polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments and mixtures thereof.

In one aspect of the aforementioned consumer product, said consumer product may comprise a total of, based on total consumer product weight, from about 0.1% to about 20%, from about 0.2% to about 15%, from about 0.3% to about 10%, from about 0.4% to about 8%, or even from about 0.5% to about 5% of one or more of the benefit agent delivery compositions of the present invention.

In one aspect of the aforementioned consumer product, said consumer product may comprise one or more of the benefit agent delivery compositions of the present invention and a material selected from the group consisting of dyes; perfume; optical brighteners; deposition aids; and mixtures thereof.

The benefit agent delivery compositions may be used in laundry detergent compositions (e.g., TIDE™), hard surface cleaners (e.g., MR CLEAN™), automatic dishwashing liquids (e.g., CASCADE™), and floor cleaners (e.g., SWIFFER™). Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Adjunct Materials

While not essential, the non-limiting list of adjuncts illustrated hereinafter are suitable for use in the instant compositions and may be desirably incorporated in certain aspects, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' agglomerate/particle. The precise nature of these additional components, and levels of incorporation thereof, will depend on the physical form of the composition and the nature of the operation for which it is to be used. Suitable adjunct materials include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The cleaning compositions can comprise one or more enzymes which provide cleaning performance and/or fabric care benefits. Examples of suitable enzymes include, but are not limited to, hemicellulases, cellulases, cellobiose dehydrogenases, peroxidases, proteases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a cleaning composition, the aforementioned additional enzymes may be present at levels from about 0.00001% to about 2%, from about 0.0001% to about 1% or from about 0.001% to about 0.5% enzyme protein by weight of the composition.

Suitable enzymes are commercially available from Genencor International Inc., Palo Alto, Calif., AB Enzymes GmbH, Darmstadt, Germany and Novozymes A/S, Bagsvaerd, Denmark and include Alcalase®, Savinase®, Primase®, Durazym®, Polarzyme®, Kannase®, Liquanase®, Ovozyme®, Neutrase®, Everlase®, Esperase®, Maxatase®, Maxacal®, Maxapem®, Properase®, Purafect®, Purafect Prime®, Purafect Ox®, FN3®, FN4®, Excellase® and Purafect OXP®, DURAMYL®, LIQUEZYME® TERMAMYL®, TERMAMYL ULTRA®, NATALASE®, SUPRAMYL®, STAINZYME®, STAINZYME PLUS®, STAINZYME ULTRA®, FUNGAMYL®, BAN® Lipolase®, Lipolase Ultra®, Lipoprime®, Lipex®, Mannaway®, Pectaway®, Pectawash®, Purabrite®, Celluclean®, Carezyme®, Celluzyme®, Biotouch®, Endolase® and Puradax HA®.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Processes of Making and Using Compositions

The compositions of the present invention can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; 5,486,303.

Method of Use

Compositions containing the encapsulated benefit agent disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs may be optionally washed and/or rinsed, contacted with a one or more of the benefit agent delivery compositions of the present invention or a consumer product comprising one or more of the benefit agent delivery compositions of the present invention and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application should be used to determine the respective values of the parameters of Applicants' invention as such invention is described and claimed herein.

Method to Determine the Characteristic Dimension (Agglomerates and Particulates)

The particle size distribution of the benefit agent delivery composition is determined using the ASTM test method E726-01 "Particle Size Distribution of Granular Carriers and Granular Pesticides". Specifically the method should be carried out using a Tyler RoTap sieve shaker supplied with cast iron sieve stack lid with centrally mounted cork (W.S. Tyler Company, Cleveland, Ohio). At least 5 sieve sizes should be selected to cover the full particle size range of the material being analysed (step 7.1). If after sieving, more than 40 wt % of the sample is found on a single sieve then the sieve selection should be modified and the sample retested until <40 wt % is found on all sieves.

The following parameters for operation of the RoTap should be applied to step 7.4 of the method:

1) 152 taps/minute 2) 285 rpm elliptical motion

3) Cork on lid to protrude 5 mm from top of holding cup.

4) A hammer drop of 33 mm from the peak height of the hammer to the top of the cork.

5) Sieve time 5 minutes.

The data are plotted on a semi-log plot with the micron size opening of each sieve plotted against the logarithmic abscissa and the cumulative mass percent (Q3) plotted against the linear ordinate. An example of the above data representation is given in ISO 9276-1:1998, "Representation of results of particle size analysis—Part 1: Graphical Representation", Figure A.4. The seed material median particle size (D50), for the purpose of this invention, is defined as the abscissa value at the point where the cumulative mass percent is equal to 50 percent, and is calculated by a straight line interpolation between the data points directly above (a50) and below (b50) the 50% value using the following equation:

$$D50 = 10^{[\log(Da50) - (\log(Da50) - \log(Db50)) * (Qa50 - 50\%)/(Qa50 - Qb50)]}$$

where Qa50 and Qb50 are the cumulative mass percentile values of the data immediately above and below the 50th percentile, respectively; and Da50 and Db50 are the micron sieve size values corresponding to these data. The median particle size on a mass basis is considered, for purposes of the present application, to be the characteristic dimension.

Method to Determine the Characteristic Dimension (Extrudates)

The diameter of an extrudate is obtained by measurement using a micrometer while the material is at 20° C. In order to determine the mean, five representative extrudates are taken from the sample to be tested and are measured taking care to not deform the extrudates during the measuring process and the arithmetic mean of such measurements is then calculated. Such arithmetic mean is considered, for purposes of the present application, to be the characteristic dimension of the extrudates.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

Melamine Based Polyurea Capsule (80% Core/20 Wt % Wall)

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid. 125 grams of the capsule core material comprising a fragrance oil is added to the first mixture at a temperature of 45° C. to form an emulsion. The capsule wall is formed as follows: 9 grams of a corresponding capsule wall material copolymer pre-polymer (butylacrylate-acrylic acid copolymer) and 90 grams of water are combined and adjusted to pH 5.0. 28 grams of a partially methylated methylol melamine resin solution ("Cymel 385", 80% solids, Cytec) is added. This mixture is added to the above described fragrance oil-in-water emulsion with stirring at a temperature of 45° C. High speed blending is used to achieve a volume-mean particle size of 15 micron. The temperature of the mixture is gradually raised to 65° C., and is maintained at this temperature overnight with continuous stirring to initiate and complete encapsulation. To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

Example 2

Melamine Based Polyurea Capsule Containing a Chelant (80% Core/20 Wt % Wall)

A first mixture is prepared by combining 208 grams of water and 5 grams of alkyl acrylate-acrylic acid copolymer (Polysciences, Inc. of Warrington, Pa., USA). This first mixture is adjusted to pH 5.0 using acetic acid. In a separated vessel, 5 mg of ethylenediaminetetraaceticacid (EDTA) is added to a mixture of 125 grams of the capsule core material comprising a fragrance oil and mixed for 20 minutes. The second mixture is added to the first mixture at a temperature of 45° C. to form an emulsion. The ingredients to form the capsule wall material are prepared as follows: 9 grams of a corresponding capsule wall material copolymer pre-polymer (butylacrylate-acrylic acid copolymer) and 90 grams of water are combined and adjusted to pH 5.0. To this mixture is added 28 grams of a partially methylated methylol melamine resin solution ("Cymel 385", 80% solids, available from Cytec). This mixture is added to the above described fragrance oil-in-water emulsion with stirring at a temperature of 45° C. High speed blending is used to achieve a volume-mean particle size of 15 micron. The temperature of the mixture is gradually raised to 65° C., and is maintained at this temperature overnight with continuous stifling to initiate and complete encapsulation. To form the acrylic acid-alkyl acrylate copolymer capsule wall, the alkyl group can be selected from ethyl, propyl, butyl, amyl, hexyl, cyclohexyl, 2-ethylhexyl, or other alkyl groups having from one to about sixteen carbons, preferably one to eight carbons.

Example 3

A 9 kg aliquot of perfume microcapsule slurry of Examples 1 is mixed using a Eurostar mixer (IKA) with a R1382 attachment at a constant speed of 200 RPM. To the aliquot, 5.4 g of ethylenediaminedisuccinicacid (EDDS), followed by 500 g of carboxymethyl cellulose (CP Kelco) is added while mixing using the Eurostar mixer with same attachment and speed as described above. The slurry is mixed for a total of two hours or until a uniform paste is formed.

Example 4

A 9 kg aliquot of perfume microcapsule slurry of Examples 2 is mixed using a Eurostar mixer (IKA) with a R1382 attachment at a constant speed of 200 RPM. To the aliquot 500 g of carboxymethyl cellulose (CP Kelco) is added while mixing using the Eurostar mixer with same attachment and speed as described above. The slurry is mixed for a total of two hours or until a uniform paste is formed.

Example 5

1.28 kg of precipitated silica Sipernat® 22S (Degussa) is added to an F-20 paddle mixer (Forberg). The mixer is run initially for 5 seconds to distribute the silica evenly on the base of the mixer. The mixer is stopped and 8.25 kg of paste, made according to Example 2, is evenly distributed onto the powder. The mixer is then run at 120 rpm for a total of 30 seconds. Following mixing, the wet particles are dumped out of the mixer and screened using a 2000 micron sieve to remove the oversize. The product passing through the screen is dried in 500 g batches in a CDT 0.02 fluid bed dryer (Niro) to a final moisture content of 20 wt % measured by Karl Fischer. The dryer is operated at an inlet temperature of 140° C. and air velocity of 0.68 m/s.

Examples 6-13

Examples of laundry detergent compositions comprising the perfume composition are included below.

| Raw material | % w/w of laundry detergent compositions | | | | | | | |
|---|---|---|---|---|---|---|---|---|
| | 6 | 7 | 8 | 9 | 10 | 11 | 12 | 13 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Benefit agent composition of Example 3 | 1.4 | 0.6 | 0.8 | 1.0 | 0.7 | 0.3 | 0.7 | 1.2 |
| Water & Miscellaneous | Balance to 100% | | | | | | | |

The equipment and materials described in Examples 1 through to 13 may be obtained from the following: IKA Werke GmbH & Co. KG, Staufen, Germany; CP Kelco, Atlanta, United States; Forberg International AS, Larvik, Norway; Degussa GmbH, Düsseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., New Jersey, United States; International Specialty Products, Wayne, N.J., United States; P&G Chemicals Americas, Cincinnati, Ohio, United States; Sigma-Aldrich Corp., St. Louis, Mo., United States.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A benefit agent delivery composition comprising an agglomerate, particulate and/or extrudate, said agglomerate, particulate and/or extrudate comprising chelant and an encapsulated benefit agent having a core and a shell encapsulating said core, said encapsulated benefit agent comprising chelant in its core; wherein said encapsulated benefit agent comprises a perfume microcapsule.

2. A benefit agent delivery composition according to claim 1 comprising an agglomerate, particulate and/or extrudate comprising, based on total weight of the benefit agent composition:
   a) from about 2% to about 97% of an encapsulated benefit agent, said encapsulated benefit agent comprising a core and a shell encapsulating said benefit agent, said encapsulated benefit agent comprising a sufficient amount of benefit agent to provide, based on total benefit delivery composition weight, from about 1% to about 85% benefit agent;
   b) a chelant, said chelant being present in said benefit agent delivery composition and in said core of said encapsulated benefit agent;
   c) from about 1% to about 50% of a plasticizer;
   d) from about 1% to about 50% a binder; and
   e) optionally, from about 1% to about 50% of a dusting agent.

3. A benefit agent delivery composition according to claim 1, wherein said perfume microcapsule comprises a shell, said shell comprising cross-linked melamine formaldehyde.

4. A benefit agent delivery composition according to claim 1, comprising an encapsulated benefit agent comprising a perfume comprising an aldehyde.

5. A benefit agent delivery composition according to claim 1, wherein said chelant comprises a chelant selected from the group consisting of chelants comprising a polidentate comprising a soft base; chelants comprising a polidentate that does not comprise a soft base; a peptide and/or a polar amino acid; and combinations thereof.

6. A benefit agent delivery composition according to claim 5, wherein said chelant comprising a polidentate is a material selected from the group consisting of ethylenediaminetetraacetic acid (EDTA), diethylenetriaminepenta(methylene phosphonic acid) (DTPMP), diethylenetriaminepentaacetic acid (DTPA), ethylenediamine, diethylene triamine, ethylenediaminedisuccinic acid (EDDS), and combinations thereof, preferably ethylenediaminedisuccinic acid.

7. A benefit agent delivery composition according to claim 5, wherein said chelant comprising a polidentate that does not comprise a soft base comprises a material selected from the group consisting of acrylic polymers; ascorbic acid; citric acid; dicarboxymethylglutamic acid; malic acid; nitrilotriacetic acid; oxalic acid; phosphoric acid; succinic acid; and combinations thereof.

8. A benefit agent delivery composition according to claim 5, wherein said chelant comprises a polar amino acid.

9. The benefit agent delivery composition of claim 2, wherein said plasticizer comprises a material selected from the group consisting of water; alcohols; glycols; fatty acids; petroleum derivatives; vegetable oils; and mixtures thereof.

10. The benefit agent delivery composition of claim 2, wherein:
   a.) said perfume microcapsule comprises a shell, said shell comprising cross-linked melamine formaldehyde and a chelating agent;
   b.) said plasticizer comprises water;
   c.) said binder is selected from the group consisting of carboxymethyl cellulose and derivatives thereof; alginate and derivatives thereof; starches; polyvinyl alcohols; polyethylene oxide; polyvinylpyrrolidone; chitosan and/or natural gums; cross-linked polyacrylates; waxes; polyethylene glycols; alcohol ethoxylates; surfactants; and mixtures thereof; and
   d.) said dusting agent is selected from the group consisting of silicas; zeolites;
   amorphous aluminosilicates; clays; starches; celluloses; water soluble salts;
   polysaccharides; and mixtures thereof.

11. The benefit agent delivery composition of claim 1, said benefit agent delivery composition being an agglomerate, extrudate or particulate, said agglomerate, extrudate or particulate having a characteristic dimension of about 100 microns to about 3000 microns wherein for said agglomerates and particulates said characteristic dimension is the median particle size of said agglomerates and particulates and the characteristic dimension of said extrudates is the mean diameter of said extrudates.

12. A consumer product comprising the benefit agent delivery composition of claim 1 and a consumer product adjunct.

13. The consumer product of claim 12, wherein said consumer product adjunct is selected from the group consisting of polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments, and mixtures thereof.

14. A consumer product comprising, based on total consumer product weight, from about 0.1% to about 20% of the benefit agent delivery composition of claim 1.

15. A method of treating and/or cleaning a situs, said method comprising
   a.) optionally washing and/or rinsing said situs;
   b.) contacting said situs with a composition according to claim 1; and
   c.) optionally washing and/or rinsing said situs.

16. A process of producing a benefit agent delivery composition according to claim 2, said process comprising:
   a.) combining an encapsulated benefit agent, said encapsulated benefit agent comprising a core and a shell encapsulating said core, said encapsulated benefit agent's core comprising perfume chelant, a plasticizer, and a binder to form a mixture;
   b.) combining said mixture with said dusting agent to form a material; and
   c.) removing a sufficient amount of said plasticizer from said material to yield a product comprising, based on total product weight from about 1% to about 50% plasticizer.

* * * * *